United States Patent [19]

Mayer et al.

[11] 4,051,252

[45] Sept. 27, 1977

[54] 3-AMINOINDAZOLE-1 AND 2-CARBOXYLIC ACID DERIVATIVES

[75] Inventors: Karl Heinrich Mayer; Siegfried Petersen; Erich Klauke, all of Leverkusen; Friedrich Hoffmeister; Wolfgang Wuttke, both of Wuppertal-Elberfeld, all of Germany

[73] Assignee: Bayer Aktiengesellschaft, Germany

[21] Appl. No.: 634,914

[22] Filed: Nov. 24, 1975

[30] Foreign Application Priority Data

Dec. 13, 1974 Germany .......................... 2458965

[51] Int. Cl.$^2$ .................. A61K 31/415; C07D 231/56
[52] U.S. Cl. .................................. 424/273 P; 548/359
[58] Field of Search .................... 260/310 C; 424/273

[56] References Cited

U.S. PATENT DOCUMENTS

| | | |
|---|---|---|
| 3,133,081 | 5/1964 | Lafferty et al. ........................ 424/273 |
| 3,274,203 | 9/1966 | Dickinson, Jr. ....................... 424/273 |
| 3,520,901 | 7/1970 | Massaroli .............................. 424/273 |
| 3,711,506 | 1/1973 | Wagner et al. ................... 260/310 C |

FOREIGN PATENT DOCUMENTS 397,698  2/1966  Switzerland .................... 260/310 C

*Primary Examiner*—Donald B. Moyer
*Attorney, Agent, or Firm*—Jacobs & Jacobs

[57] ABSTRACT

3-Aminoindazoles bearing a carbo(lower alkoxy), lower alkylamide or di(lower alkyl)amide group in the 1-or 2-position and further being optionally substituted in one or more of the 4-, 5-, 6- and/or 7-positions are analgesic, anti-inflammatory and antipyretic agents. The compounds, of which 3-amino-6-chloroindazole-1-carboxylic acid ethyl ester is a typical embodiment, are prepared through treatment of the appropriate 3-aminoindazole with a derivative of carbonic acid or through thermal isomerization.

30 Claims, No Drawings

3-AMINOINDAZOLE-1 AND 2-CARBOXYLIC ACID DERIVATIVES

DETAILED DESCRIPTION

The present invention pertains to new 3-aminoindazolecarboxylic acid derivatives, processes for their preparation and use, and to pharmaceutical compositions for achieving analgesic, anti-inflammatory and antipyretic effects.

Certain 3-aminoindazoles have been described in German Published Specification No. 1,280,878 as analgesics and antipyretics, 3-amino-5-trifluoromethylindazole being particularly singled out as having especially advantageous therapeutic properties. 3-Aminoindazoles are also known in dyestuff chemistry where they are useful as starting materials. (See German Published Specification No. 1,149,839).

The present invention pertains to compounds selected from the group consisting of 3-aminoindazole-1- and -2-carboxylic acid derivatives of the formulas:

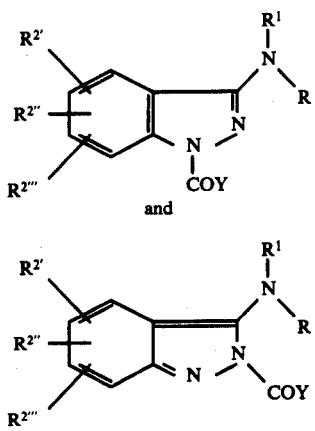

wherein
Y is lower alkoxy, lower alkylamino or di(lower alkyl)amino;
R is hydrogen or lower alkyl;
$R^1$ is hydrogen or lower alkyl or, where R is hydrogen, formyl; and
each of $R^{2'}$, $R^{2''}$ and $R^{2'''}$ is selected, independently of the others, from the group consisting of hydrogen, lower alkyl, lower alkoxy, nitro, amino, lower alkylamino, di(lower alkyl)amino, lower alkanoylamino, carbo(lower alkoxy)amino, halo, trifluoromethyl, cyano and carbo(lower alkoxy),
and the pharmaceutically acceptable nontoxic salts thereof.

The foregoing compounds of Formulas IA and IB and their salts demonstrate valuable action of the central nervous system, in particular excellent analgesic, antipyretic and anti-inflammatory properties. Surprisingly, these 3-aminoindazole-1-and -2-carboxylic acid derivatives demonstrate better toleration and a substantially greater analgesic, antipyretic and antiphlogistic- (anti-edematous) action than known aminoindazoles such as 3-amino-5-trifluoromethylindazole, which might be deemed chemically to be the closest related compound.

In the context of the present specification and claims, the term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

Lower alkanoyl denotes the residue of a straight or branched alkanoic acid of from 1 to 6 carbon atoms such as formyl, acetyl, propionyl, butyryl, isobutyrlyl, valeroyl, isovaleroyl, pivaloyl and the like.

The term halo denotes the monovalent substituents fluoro, chloro, bromo and iodo. As a substituent, chloro, fluoro or bromo, particularly chloro, is preferred. As a reactive nucleofugic group as in alkylating or acylating reagents, chloro or bromo is preferred.

In a first preferrerd embodiment, the invention pertains to the two classes of compounds depicted by Formulas IA and IB wherein both of R and $R^1$ are hydrogen, both of R and $R^1$ are methyl or R is hydrogen and $R^1$ is formyl.

A further embodiment pertains to those compounds wherein each of $R^{2'}$, $R^{2''}$ and $R^{2'''}$ is selected, independently of the others, from the group consisting of hydrogen, chloro, trifluoromethyl, nitro, amino, cyano, lower alkyl or carbo(lower alkoxy) amino.

Still a further embodiment pertains to compounds wherein each of $R_{2'}$ and $R^{2'''}$ is hydrogen and $R^{2''}$ is chloro or trifluoromethyl. Within this embodiment a preferred class entails those compounds wherein $R^{2''}$ is chloro trifluoromethyl in the 5- or 6-position of the indazole ring.

A further embodiment pertains to compounds wherein Y is methoxy, ethoxy, propoxy, or butoxy.

A further embodiment pertains to those compounds wherein Y is methylamino, ethylamino, dimethylamino or diethylamino.

The compounds of the present invention can be prepared in a number of ways. A 3-aminoindazole, which can be diagrammatically depicted by the tautomeric formulas:

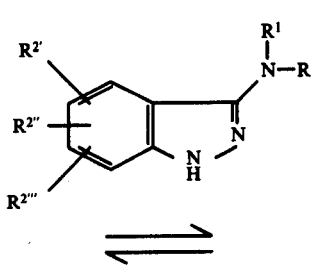

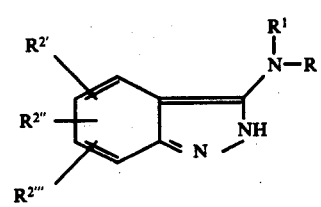

can be treated with
i. a halocarbonic acid lower alkyl ester or di(lower alkali)pyrocarbonate to yield a 3-aminoindazole-1- or -2-carboxylic acid derivative wherein Y is lower alkoxy;

ii. a lower alkyl isocyanate to yield a 3-aminoindazole-1- or -2-carboxylic acid derivative wherein Y is lower alkylamino; or conventional methods, e.g. bismethylation with formaldehyde and formic acid.

The following typifies the foregoing reactions:

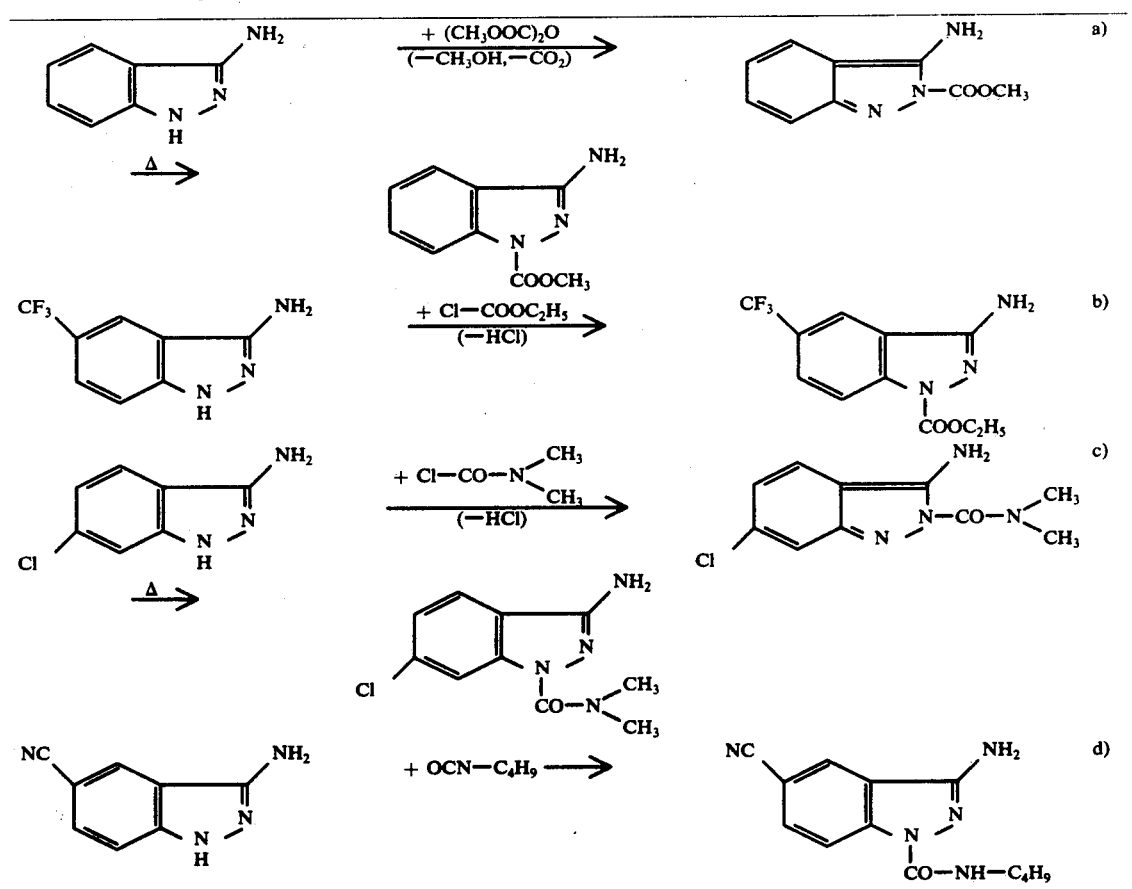

iii. a di(lower alkyl) carbamic acid halide to yield a 3-aminoindazole-1- or -2-carboxylic acid derivative The course of a subsequent bismethylation is typified by the following:

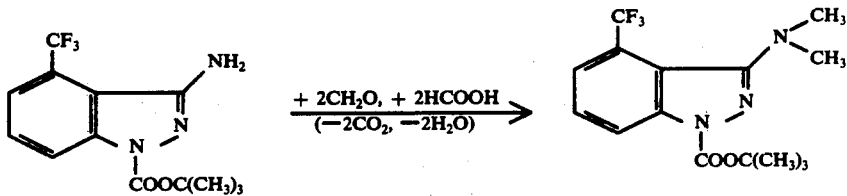

wherein Y is di(lower alkyl) amino.

As is apparent from the foregoing, both the 1-carboxylic acid derivatives and isomeric 2-carboxylic acid derivatives can be obtained according to these methods. The relative proportions of the two isomeric forms depicted by Formulas IA and IB are dependent on temperature. At lower temperatures, e.g. 0°–50° C, the 2-carboxylic acid derivatives are preferentially formed although some of the corresponding 1-carboxylic acid derivatives can also be formed, whereas at higher temperatures, e.g. 80° to 130° C, the 1-carboxylic acid derivative is preferentially formed.

Moreover, by subjecting the 2-carboxylic acid derivative to even higher temperatures, it can be converted through isomerization to the corresponding 1-carboxylic acid derivative.

Finally, compounds of Formulas IA and IB in which R and R¹ are hydrogen can be alkylated according to The 3-aminoindazoles of Formulas IIA and IIB used as starting materials are known or can be readily prepared according to known processes, see e.g. J. Amer. chem. Soc. 65 (1943), 1804, J. chem. Soc. (London) 1959, 2363 and Liebigs Ann. Chem. 716 (1968), 47. The following are typical examples: 3-aminoindazole, 3-amino-4-methylindazole, 3-amino-5-isopropylindazole, 3-amino-6-n-butylindazole, 3-amino-4,7-dimethylindazole, 3-amino-5,6-diethylindazole, 3-amino-5-ethyl-6-isopropylindazole, 3-amino-6-methoxyindazole, 3-amino-4-methyl-7-n-propoxyindazole, 3-amino-nitroindazole, 3-amino-5,7-dinitroindazole, 3,5-diaminoindazole, 3,5,7-triaminoindazole, 3,5-diamino-7-nitroindazole, 3-amino-5-methylaminoindazole, 3-amino-5-t-butylaminoindazole, 3-amino-5-dimethylaminoindazole, 3-amino-5-formylaminoindazole, 3-amino-5,7-bisformylaminoindazole, 3-amino-5-acetylaminoindazole, 3-amino-5-pivaloylaminoindazole, 3-amino-4-chloroindazole, 3,-amino-5-chloroindazole, 3-amino-6-chloroindazole, 3-amino-5-bromoindazole, 3-amino-6-fluoroindazole, 3-amino-4,7-dichloroindazole, 3-amino-4-methyl-6-chloroindazole, 3-amino-4-ethyl-5-bromoindazole, 3-amino-4-ethoxy-6-chloroindazole, 3-amino-4-trifluoromethylindazole, 3-amino-5-trifluoromethylindazole, 3-amino-6-trifluoromethylindazole, 3-amino-7trifluoromethylindazole, 3-amino-5-trifluoromethyl-6-ethylindazole, 3-amino-5-methoxy-6-trifluoromethylindazole, 3-amino-5-trifluoromethyl-7-nitroindazole, 2,7-diamino-5-trifluoromethylindazole, 3-amino-5-trifluoromethyl-7-n-butylaminoindazole, 3-amino-5-trifluoromethyl-7-isopropionylaminoindazole, 3-amino-5-cyanoindazole, 3-amino-5-cyano-7-nitroindazole, 3-amino-5-cyano-7-formylaminoindazole, 3-amino-5-carboethoxyindazole, 3-amino-5-carbobutoxyindazole, 3-formylaminoindazole, 3-methylaminoindazole, 3-dimethylaminoindazole, 3-formylamino-5-ethylindazole, 3-dimethylamino-6-ethoxyindazole, 3-dimethylamino-5,6-dimethoxyindazole, 3-formyl-5-nitroindazole, 3-methylamino-5-aminoindazole, 3-dimethylamino-6-chloroindazole, 3-formylamino-5-trifluoromethylindazole. 3-amino-5-ethoxyindazol and 3-amino-5,6-dimethoxyindazol.

The carbonic acid derivatives using as starting materials are similarly known or can be readily prepared by the known method. Pyrocarbonic acid esters include pyrocarbonic acid methyl ester, pyrocarbonic acid ethyl ester, pyrocarbonic acid propyl ester, pyrocarbonic acid isopropyl ester and pyrocarbonic acid butyl ester; see e.g. Liebigs Ann. Chem. 624, pages 30–36 (1959). Chlorocarbonic acid esters include chlorocarbonic acid methyl ester, chlorocarbonic acid ethyl ester, chlorocarbonic acid propyl ester, chlorocarbonic acid isopropyl ester and chlorocarbonic acid butyl ester; see e.g. Beilsteins Handbuch der Organischen Chemie, edition IV, 3rd supplement, volume 3, pages 23–26. Carbamic acid halides include dimethylcarbamic acid chloride, dimethylcarbamic acid bromide, diethylcarbamic acid chloride, methylethylcarbamic acid chloride, methylethylcarbamic acid bromide, dipropylcarbamic acid bromide, diisopropylcarbamic acid chloride and dibutylcarbamic acid bromide; see e.g. Beilsteins Handbuch der Organischen, edition IV, 3rd supplement, volume 4, pages 144, 222 and 301. The carbonic acid imides or isocyanates include methyl isocyanate, ethyl isocyanate, propyl isocyanate, isopropyl isocyanate, n-butyl isocyanate and tert-butyl isocyanate; see e.g. Beilsteins Handbuch der Organischen Chemie, edition IV, 3rd supplement, volume 4, pages 156, 227, 263, 279, 303, 321 and 325.

Diluents optionally can be used and include all organic solvents which are inert towards the particular reactants. These include aliphatic alcohols such as methanol, ethanol, isopropanol or butanol; hydrocarbons such as benzene, toluene and xylene; halohydrocarbons such as chloroform, carbon tetrachloride, chlorobenzene and dichlorobenzenes; carboxylic acid esters such as ethyl acetate; nitriles such as acetonitrile and propionitrile; ketones such as acetone and methyl isobutyl ketone; ethers such as tetrahydrofuran or dioxane; carboxylic acid amides such as dimethylformamide or dimethylacetamide; and heterocyclic bases such as pyridine, picolines, lutidiens, collidines, quinoline or isoquinoline, as well as mixtures of these solvents. When pyrocarbonic acid esters are employed, one can utilize an excess which serves as both solvent and reactant.

Suitably 100 to 1,000 ml of the diluent are employed per mol of the 3-aminoindazole of Formulas IIA and IIB.

The reaction can be carried out under elevated pressure but in general, it is carried out under normal pressure. The starting materials as a rule dissolve entirely or partially in the reaction mixture while the end products generally crystallize. Separation of the products can be accelerated by cooling and/or by adding such precipitants as ethers, for example diethyl ether or dibutyl ether, or aliphatic hydrocarbons, for example petroleum ether, light benzene or ligroin, or halohydrocarbons, for example carbon tetrachloride. The reaction temperatures can be varied within a substantial range and in general, temperatures between −20° and +250° C, preferably between −10° and 100° C, especially between 0° and 50° C, are used.

Acid binding agents can be used and include include inorganic bases such as alkali metal hydroxides, for example calcium hydroxide or barium hydroxide, alkali metal carbonates or alkaline earth metal carbonates such as sodium carbonate, potassium carbonate, calcium carbonate or sodium bicarbonate, amides such as sodamide, and organic bases such as tertiary amines, for example triethylamine, N,N-dimethylaniline, pyridines, quinolines and isoquinolines. The use of pyridines, lutidines and collidines or quinoline as the acid binding agent is particularly advantageous since these can also serve as the diluent or solvent.

The thermal rearrangement of the 2-carboxylic acid derivatives to the 1-carboxylic acid derivatives can be effected by simply heating in the absence of solvents to temperatures above their melting point, or by heating them in the presence of solvents. Solvents for the latter rearrangement procedure include all inert higher-boiling organic solvents, especially ethers such as diethylene glycol dimethyl ether, diethylene glycol diethyl ether and diethylene glycol dibutyl ether; carboxylic acid amides such as dimethylformamide and dimethylacetamide; aromatic hydrocarbons or aromatic hydrocarbon derivatives, such as xylene, tetralin, chlorobenzene, dichlorobenzenes, nitrobenzene or anisole; or heterocyclic bases such as pyridine, picolines, lutidines, collidines, quinoline and isoquinoline. The heterocyclic bases are particularly suitable, as are mixtures of these bases with other organic solvents. The reaction temperatures for this rearrangement will vary within a substantial range depending on the specific compound. In general, the rearrangement is carried out at temperatures between 20° and 250° C, preferably between 50° and 200° C, and especially between 100° and 170° C.

The formylation or methylation of the $NH_2$- group in the 3-position in Formulas LA and IB is carried out by heating with formic acid or a mixture of formaldehyde and formic acid at temperatures around 100° C.

The following may be mentioned individually as new active compounds: 3-amino-indazole-1-carboxylic acid methyl ester, 3-amino-indazole-2-carboxylic acid ethyl ester, 3-aminoindazole-1-carboxylic acid n-butylamide, 3-amino-indazole-2-carboxylic acid dimethylamide, 3-dimethylamino-indazole-1carboxylic acid ethyl ester, 3-formylamino-indazole-1-carboxylic acid n-butyl ester, 3-amino-5-methyl-indazole-1-carboxylic acid diethylamide, 3-amino-5,6-bis-methoxy-indazole-1-carboxylic acid ethyl ester, 3-amino-5,6-bis-methoxy-indazole-2-carboxylic acid ethyl ester, 3-formylamino-5-nitroindazole-1-carboxylic acid i-propylamide, 3-amino-5-ethoxycarbonylaminoindazole-1-carboxylic acid ethyl ester, 3-amino-5,7-bis-ethoxycarbonylamino-indazole-1- carboxylic acid ethyl ester, 3-amino-4-chloro-indazole-2-carboxylic acid methyl ester, 3-amino-5-chloro-indazole-1-carboxylic acid n-propylamide, 3-amino-5-chloro-indazole-1-carboxylic acid dimethylamide, 3-dimethylamino-5-chloro-indazole-1-carboxylic acid n-propyl ester, 3-formylamino-indazole-1-carboxylic acid ethylamide, 3-amino-6-chloro-indazole-1-carboxylic acid methyl ester, 3-amino-6-chloroindazole-1-carboxylic acid ethyl ester, 3-amino-6-chloro-indazole-2-carboxylic acid ethyl ester, 3-amino-6-chloro-indazole-1-carboxylic acid n-butyl ester, 3-amino-6-chloro-indazole-1-carboxylic acid dimethylamide, 3-amino-6-chloro-indazole-2-carboxylic acid dimethylamide, 3-amino-6-chloro-indazole-1-carboxylic acid n-butylamide, 3-dimethylamino-6-chloro-indazole-1-carboxylic acid ethyl ester, 3-formylamino-6-chloro-indazole-1-carboxylic acid di-n-propylamide, 3-amino-4,7-dichloro-indazole-1-carboxylic acid ethyl ester, 3-amino-5-bromo-indazole-1-carboxylic acid dimethylamide, 3-amino-6-fluoro-indazole-1-carboxylic acid t-butyl ester, 3-amino-4-trifluoromethyl-indazole-1-carboxylic acid methyl ester, 3-amino-4-trifluoromethyl-indazole-2-carboxylic acid dimethyl-amide, 3-amino-5-trifluoromethyl-indazole-1-carboxylic acid methyl ester, 3-amino-5-trifluoromethyl-indazole-2-carboxylic acid methyl ester, 3-amino-5-trifluoromethylindazole-1-carboxylic acid ethyl ester, 3-amino-5-trifluoromethyl-indazole-2-carboxylic acid ethyl ester, 3-amino-5-trifluoromethyl-indazole-1-carboxylic acid i-butyl ester, 3-amino-5-trifluoro-methyl-indazole-1-carboxylic acid dimethylamide, 3-amino-5-trifluoromethyl-indazole-1-carboxylic acid n-butylamide, 3-methylamino-5-trifluoromethyl-indazole-1-carboxylic acid ethyl ester, 3-dimethylamino-5-trifluoromethyl-indazole-1-carboxylic acid di-n-butylamide, 3-formylamino-5-trifluoromethyl-indazole-1-carboxylic acid n-propylamide, 3-amino-5-trifluoromethyl-7-ethoxycarbonylamino-indazole-1-carboxylic acid ethyl ester, 3-amino-5-cyano-indozole-2-carboxylic acid methyl ester and 3-amino-5-n-butoxycarbonylamino-indazole-1-carboxylic acid n-butylamide.

As indicated, the present invention also pertains to the physiologically acceptable salts of the foregoing compounds with alkali metals, alkaline earth metals, ammonia and organic amines as, for example, the sodium salt, the potassium salt, the calcium salt, and the salts with amines such as ethylamine, triethylamine, ethanolamine, diethylaminoethanol, ethylenediamine, piperidine, morpholine, 2-piperidinoethanol, benzylamine, procaine and the like.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

In the case of parenteral application a fact which has proved particularly advantageous is that the compounds according to the invention form readily water-soluble salts. These salts are obtained when the compounds according to the invention, in a suitable solvent, are combined with the equimolar amount of a nontoxic inorganic or organic base, as described above. Particularly preferred bases for this purpose are sodium hydroxide, potassium hydroxide, ethanolamine, diethanolamine, triethanolamine, amino-tris-hydroxymethylmethane, glucosamine and N-methyl-glucosamine. Such salts can also be of importance for oral administration in that they accelerate or delay the resorption, as desired. In addition to the salts described above, the magnesium, aluminium and iron salts are also useful.

The present invention thus includes pharmaceutical compositions comprising a compound of Formula IA or IB in combination with a pharmaceutical carrier. The amount of the compound present in the composition is at least that calculated to be sufficient upon single or multiple administration to a human or other warm blooded animal to achieve an analgesic, anti-inflammatory or antipyretic effect. The method of achieving such effects in the human or other warm blooded animal through administration is also within the scope of the present invention.

In general, a suitable effect is observed in the case of parenteral administration at daily doses of from about 0.01 to about 50 mg/kg, preferably about 0.1 to about 10 mg/kg, of body weight. In the case of oral administration, the daily dosage is about 0.1 to about 500 mg/kg, preferably about 0.5 to about 100 mg/kg, of body weight. Nevertheless, at times it can be necessary to deviate from these ranges and in particular to do so as a function of the body weight, the nature of the administration route, the species, response, the nature of the formulation, and the time or interval of administration. In some cases less than the above mentioned minimum amount while in others the upper limit must be exceeded. Where large amounts are administered it is advisable to divide these into several individual administrations over the course of the day.

The pharmacological properties can be conveniently observed in recognized in vivo models. As can be seen from the following, the acute toxicity of these compound is extremely favorable.

Table I

| Acute Toxicity | |
|---|---|
| Compound | $LD_{50}$ (oral)/mouse mg/kg |
| 3-amino-5-trifluoromethylindazole (known) | 228 (199–258) |
| 3-aminoindazole-1-carboxylic acid ethyl ester | ~ 3,000 |
| 3-amino-6-chloroindazole-1-carboxylic acid methyl ester | > 1,000 |
| 3-amino-6-chloroindazole-1-carboxylic acid ethyl ester | ~ 2,000 |
| 3-amino-6-chloroindazole-1-carboxylic acid butyl ester | > 1,000 |
| 3-amino-6-chloroindazole-1-carboxylic acid dimethylamide | > 1,000 |
| 3-dimethylamino-6-chloroindazole-1-carboxylic acid ethyl ester | > 5,000 |
| 3-formylamino-5-trifluoromethyl-indazole-1-carboxylic acid dimethylamide | > 1,000 |
| 3-amino-5-trifluoromethylindazole-1-carboxylic acid ethyl ester | > 5,000 |
| 3-amino-5-trifluoromethylindazole-1-carboxylic acid ethylamide | > 1,000 |

Analgesic action can be observed in the tail flick test on the tails of rats in which the tail of male rats is irradiated with a focused heat ray. In this test, untreated animals react after an average irradiation time of 5.1±0.8 seconds (reaction time) by drawing away the tail. Under the influence of analgesically active compounds, this reaction time becomes longer. Active compounds which after administration prolong the reaction time of the animals to at least 20 seconds are considered to be analgesically active. Five animals are employed per dose. The $ED_{50}$ is the dose which on average lengthens the reaction time of 50% of the animals employed to at least 20 seconds [see generally Wolff et al., J. Clin. Invest., 19, 659–680 (1940)].

Table II

| Tail Flick Test | |
|---|---|
| Compound | $ED_{50}$ (oral) mg/kg |
| 3-amino-5-trifluoromethylindazole (known) | 67 (19–78) |
| 3-amino-6-chloroindazole-1-carboxylic acid methyl ester | 30 (14–82) |
| 3-amino-5-trifluoromethylindazole-1-carboxylic acid methyl ester | 41 (26–65) |
| 3-amino-6-trifluoromethylindazole-1-carboxylic acid ethyl ester | 53 (31–81) |
| 3-amino-5-trifluoromethylindazole-1-carboxylic acid ethylamide | 53 (36–85) |

Analgesic activity can also be observed in the phenylquinone writhing test in which 100 μg of phenylquinone, dissolved in 0.5 ml of 5% strength alcohol, are injected intraperitoneally into rats. A few minutes after administration, the animals show the characteristic writhing reaction, which consists of the animals showing extreme backward extension of the hind paws, flexing the back and lifting the tail. At the same time, wave-like contractions frequently pass over the abdominal muscles. The inhibition of this writhing syndrome is assessed to be an analgesic effect. The substance to be investigated is administered 30 minutes (in the case of subcutaneous administration) or 60 minutes (in the case of oral administration) before the injection of phenylquinone. Five animals are employed per compound and per dose. The $ED_{50}$ is the dose at which the number of writhing reactions in the animals employed is on average reduced to half that of the control group [see generally: Siegmung et al., Proc. Soc. exp. Biol. Med. 95, 729–731 (1957)].

Table III

| Phenylquinone Writhing Test | |
|---|---|
| Compound | $ED_{50}$ (oral) mg/kg |
| 3-amino-5-trifluoromethylindazole (known) | 61 (32–79) |
| 3-amino-6-chloroindazole-1-carboxylic acid methyl ester | ~ 10 |
| 3-amino-6-chloroindazole-2-carboxylic acid dimethylamide | 17 (11–26) |
| 3-dimethylamino-6-chloroindazole-1-carboxylic acid ethyl ester | 17 (12–24) |
| 3-amino-5-trifluoromethylindazole-1-carboxylic acid ethyl ester | 1.0 (0.3–23.4) |

The anti-inflammatory (antiphlogistic and anti-edematous) action of the compounds can be conveniently observed by the inhibition of carrageenin edema on the paw of rats. In this test, a reference measurement on the normal paws of rats is carried out half an hour before and half an hour after oral administration of the test compound, using an antiphlogmeter. One hour after administration of the substance, the edema is started by injecting a carrageenin solution into the planta pedis of one hind paw at 2½ hours and 3 hours after the carrageenin injection, the effect on the edematous paw is measured. The relative paw volume is expressed as a percentage of the reference measurement (=100%). The $ED_{50}$ is the dose at which, in 50% of the animals employed per dose, the difference between the relative paw volume of the treated animals and the relative paw volume of the 10 control groups is 100.

Table IV

Carrageenin Anti-inflammatory Test

| Compound | ED$_{50}$ (oral) mg/kg |
|---|---|
| 3-amino-5-trifluoromethylindazole (known) | > 100 |
| 3-aminoindazole-1-carboxylic acid ethyl ester | ~ 47 |
| 3-amino-6-chloroindazole-1-carboxylic acid methyl ester | ~ 40 |
| 3-amino-6-chloroindazole-1-carboxylic acid ethyl ester | ~ 77 |
| 3-amino-6-chloroindazole-1-carboxylic acid butyl ester | 67 (38–117) |
| 3-amino-6-chloroindazole-1-carboxylic acid ethyl ester | 68 (44–138) |
| 3-formylamino-6-trifluoromethyl-1-carboxylic acid dimethylamide | 92 (44–216) |

Antipyretic action can be observed in rats to which a beer yeast suspension has been administered subcutaneously. The body temperature is measured rectally before and 16 hours after administration of the beer years. The substance to be tested is administered orally to groups of 5 rats in which the body temperature has risen by at least 1° C. Thereafter, the temperature drop is measured rectally with a drop in the body temperature of at least 1° C being assessed as an antipyretic effet. The Ed$_{50}$ is the dose at which, in 50% of the animals employed, the raised body temperature is lowered by 1° C upon administration of the active substance according to the invention.

Table 5

Yeast Antipyretic Test

| Compound | ED$_{50}$ (oral) mg/kg |
|---|---|
| 3-amino-5-trifluoromethylindazole (known) | 48 (32–63) |
| 3-amino-6-chloroindazole-1-carboxylic acid methyl ester | ~ 20 |
| 3-amino-6-chloroindazole-1-carboxylic acid dimethylamide | 41 (26–53) |
| 3-amino-6-chloroindazole-2-carboxylic acid dimethylamide | 23 (16–30) |
| 3-dimethylamino-6-chloroindazole-1-carboxylic acid ethyl ester | 5.2 (1.1–11) |
| 3-formylamino-5-trifluoromethylindazole-1-carboxylic acid dimethylamide | 14 (12–15) |
| 3-amino-5-trifluoromethylindazole-1-carboxylic acid methyl ester | ~ 50 |
| 3-amino-6-trifloromethylindazole-1-carboxylic acid ethyl ester | ~ 50 |
| 3-amino-5-trifluoromethylindazole-1-carboxylic acid ethylamide | 51 (28–88) |

The following examples wll serve to further typify the nature of this invention without constituting a limitation on the scope thereof. The structure of the reaction products in these examples was confirmed by elementary analysis and in part also be mass-spectrometric molecular weight determination. In the case of isomeric compounds, the consistency and position of the substituents was above all confirmed by physico-chemical methods of investigation, especially H[1]- and F[19]- nuclear resonance, IR-spectroscopy and UV-spectroscopy.

Starting materials are known or were prepared by conventional methods which can be summarized as follows:

3-Amino-4-trifluoromethylindazole (melting point: 129°–130° C) from 2,6-dimethylbenzonitrile by chlorination to give 2-chloro-6-trichloromethylbenzonitrile (melting point: 121°–122° C) and subsequent fluorination to give 2-chloro-6-trifluoromethylbenzonitrile (melting point: 45°–47° C), and reaction with hydrazine hydrate in dioxane at 150° C in an autoclave.

3-Amino-7-trifluoromethylindazole (melting point: 101°–102° C) from 2,3-dimethylbenzonitrile by chlorination to give 2-chloro-3-trichloromethylbenzonitrile (melting point: 106°–107° C) and fluorination to give 2-chloro-3-trifluoromethylbenzonitrile (melting point: 37°–39° C), and reaction with hydrazine hydrate in dioxane at 150° C in an autoclave.

3-Amino-5-trifluoromethyl-7-nitroindazole (melting point: 227°–228° C) from 2-methoxy-3-nitro-5-trifluoromethylbenzonitrile and hydrazine hydrate, analogously to J. chem. Soc. [London] 1959, 2363.

3,7-Diamino-5-trifluoromethylindazole (melting point: 198°–199° C) from 3-amino-5-trifluoromethyl-7-nitroindazole by catalytic hydrogenation with Raney nickel in dimethylformamide at 50° C.

3Amino-5-cyanoindazole (melting point: 224°–225° C) from 4-chloro-isophthalic acid dinitrile and hydrazine hydrate analogously to J. chem. Soc. [London] 1959, 2263.

3-Dimethylamino-6-chloroindazole (melting point: 131°–132° C) from 3-dimethylamino-6-chloroindazole-1-carboxylic acid ethyl ester and 10% strength sodium hydroxide solution in methanol at pH 10 and 20° C.

3-Dimethylamino-5-trifluoromethylindazole (melting point: 193°–196° C) from 3-dimethylamino-5-trifluoromethylindazole-1-carboxylic acid ethyl ester and 10% strength sodium hydroxide solution in methanol at pH 10 and 20° C.

3-Amino-4,6-dimethyl-5-cyanoindazole (melting point: 260°–262° C) from 2-amino-4,6-dimethyl-5-cyanobenzonitrile by diazotization and subsequent reduction with sulphurous acid.

EXAMPLE 1

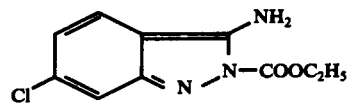

0.3 mol of 3-amino-6-chloroindazole in 250 ml of pyrocarbonic acid diethyl ester are heated, while stirring, to 50° C for about 5 hours, until the evolution of CO$_2$ has ceased. After cooling, 250 ml of diethyl ether are added and 90% of theory of 3-amino-6-chloroindazole-2-carboxylic acid ethyl ester are isolated, by filtration, in the form of yellow crystals. Melting point: 163°–165° C.

EXAMPLE 2

The reaction product of Example 1 is also obtained, in 80% yield, on reacting 0.1 mol of 3-amino-6-chloroindazole and 0.15 mol of pyrocarbonic acid diethyl ester in 50 ml of ethanol in 2 hours at 50° C.

EXAMPLE 3

The reaction product of Example 1 is also obtained, in 65% yield, on reacting 0.2 mol of 3amino 6-chloroindazole, 0.22 mol of chlorocarbonic acid ethyl ester and 0.22 mol of sodium bicarbonate in 150 ml acetone in 3 hours at 20°–30° C.

EXAMPLE 4

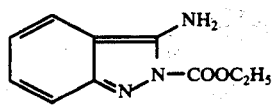

Analogously to Example 1, 0.01 mol of 3-aminoindazole and 0.01 mol of pyrocarbonic acid diethyl ester in 20 ml of dimethylformamide give 3-aminoindazole-2-carboxylic acid ethyl ester (melting point: 182°–183° C; 78% of theory) in 15 minutes at 5°–10° C.

EXAMPLE 5

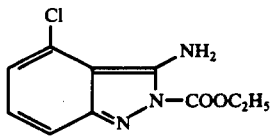

Analogously to Example 1, 0.2 mol of 3-amino-4-chloroindazole in 100 ml of pyrocarbonic acid diethyl ester gives 3-amino-4-chloroindazole-2-carboxylic acid ethyl ester (melting point: 109°–111° C; 63% of theory) in 3 hours at 20°–30° C.

EXAMPLE 6

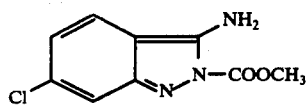

Analogously to Example 1, 0.1 mol of 3-amino-6-chloroindazole in 50 ml of pyrocarbonic acid dimethyl ester gives 3-amino-6-chloroindazole-2-carboxylic acid methyl ester (melting point: 198°–200° C; 90% of theory) in 30 minutes at 30°–50° C.

EXAMPLE 7

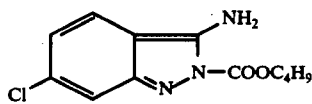

Analogously to Example 1, 0.05 mol of 3-amino-6-chloroindazole and 0.075 mol of pyrocarbonic acid di-n-butyl ester give 3-amino-6-chloroindazole-2-carboxylic acid n-butyl ester (melting point: 169°–170° c; 81% of theory) in 5 hours at 50° C.

EXAMPLE 8

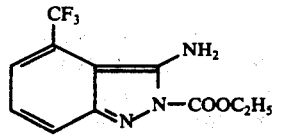

Analogously to Example 1, 0.06 mol of 3-amino-4-trifluoromethylindazole in 50 ml of pyrocarbonic acid diethyl ester gives 3-amino-4-trifluoromethylindazole-2-carboxylic acid ethyl ester (melting point: 100°–101° C; 85% of theory) in 10 minutes at 20° C.

EXAMPLE 9

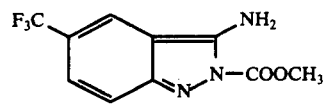

Analogously to Example 1, 0.1 mol of 3-amino-5-trifluoromethyl-indazole in 50 ml of pyrocarbonic acid dimethyl ester gives 3-amino-5-trifluoromethylindazole-indazole-2-carboxylic acid methyl ester (melting point: 164°–165° C; 64% of theory) in 2 hours at 50° C.

EXAMPLE 10

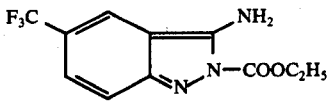

Analogously to Example 1, 0.1 mol of 3-amino-5-trifluoromethylindazole and 0.125 mol of pyrocarbonic acid diethyl ester in 100 ml of ethanol give 3-amino-5-trifluoromethylindazole-2-carboxylic acid ethyl ester (melting point: 182°–184° C; 82% of theory) in 1 hour at 80° C.

EXAMPLE 11

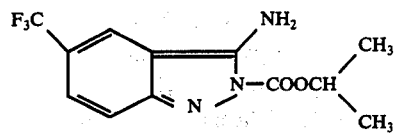

Analogously to Example 1, 0.05 mol of 3-amino-5-trifluoromethylindazole and 0.055 mol of pyrocarbonic acid di-isopropyl ester give 3-amino-5-trifluoromethylindazole-2-carboxylic acid isopropyl ester (melting point: 184°–186° C; 82% of theory) in 5 minutes at 20°–30° C.

EXAMPLE 12

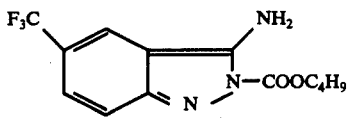

Analogously to Example 1, 0.05 mol of 3-5-trifluoromethylindazole and 0.055 mol of pyrocarbonic acid di-n-butyl ester give 3-amino-5-trifluoromethylindazole-2-carboxylic acid n-butyl ester (melting point: 147°–149° C; 73% of theory) in 5 minutes at 20°–30° C.

EXAMPLE 13

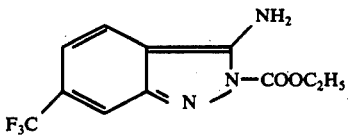

Analogously to Example 1, 0.04 mol of 3-amino-6-trifluoromethylindazole and 50 ml of pyrocarbonic acid diethyl ester in 25 ml of ethanol give 3-amino-6-trifluoromethylindazole-2-carboxylic acid ethyl ester

EXAMPLE 14

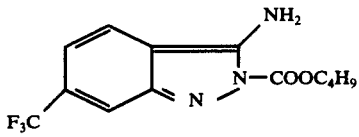

Analogously to Example 1, 0.05 mol of 3-amino-6-trifluoromethylindazole and 0.055 mol of pyrocarbonic acid di-n-butyl ester give 3-amino-6-trifluoromethylindazole-2-carboxylic acid n-butyl ester (melting point: 139°–140° C; 93% of theory) in 1 hour at 50° C.

EXAMPLE 15

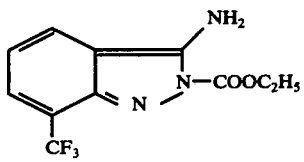

Analogously to Example 1, 0.05 mol of 3-amino-7-trifluoromethylindazole and 0.055 mol of pyrocarbonic acid diethyl ester give 3-amino-7-trifluoromethylindazole-2-carboxylic acid ethyl ester (melting point: 174°–175° C; 93% of theory) in 5 minutes at 20°–25° C.

EXAMPLE 16

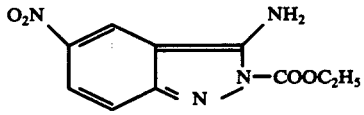

Analogously to Example 1, 0.2 mol of 3-amino-5-nitroindazole and 0.22 mol of pyrocarbonic acid diethyl ester in 100 ml of dimethylformamide give 3-amino-5-nitroindazole-2-carboxylic acid ethyl ester (melting point: 226°–227° C; 76% of theory) in 8 hours at 10°–20° C.

EXAMPLE 17

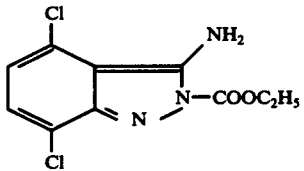

Analogously to Example 1, 0.15 mol of 3-amino-4,7-dichloroindazole in 100 ml of pyrocarbonic acid diethyl ester gives 3-amino-4,7-dichloroindazole-2-carboxylic acid ethyl ester (melting point: 143°–145° C; 69% of theory) in 5 hours at 50° C.

EXAMPLE 18

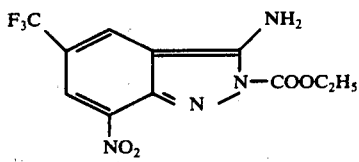

Analogously to Example 1, 0.1 mol of 3-amino-5-trifluoromethyl-7-nitroindazole and 150 ml of pyrocarbonic acid diethyl ester in 100 ml of ethanol give 3-amino-5-trifluoromethyl-7-nitro indazole-2-carboxylic acid ethyl ester (melting point: 186°–187° C; 74% of theory) in 30 minutes at 80° C.

EXAMPLE 19

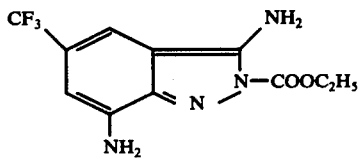

Analogously to Example 1, 0.1 mol of 3.7-diamino-5-trifluoromethylindazole in 70 ml of pyrocarbonic acid diethyl ester gives 3,7-diamino-5-trifluoromethylindazole-2-carboxylic acid ethyl ester (melting point: 193°–194° C; 90% of theory) in 1 hour at 20°–30° C.

EXAMPLE 20

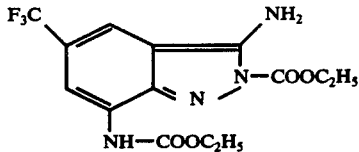

Analogously to Example 1, 0.1 mol of 3,7-diamino-5-trifluoromethylindazole in 70 ml of pyrocarbonic acid diethyl ester gives 3-amino-5-trifluoromethyl-7-ethoxycarbonylaminoindazole-2-carboxylic acid ethyl ester (melting point: 229°–230° C; 89% of theory) in 20 minutes at 70° C.

EXAMPLE 21

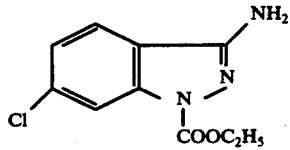

0.1 mol of 3-amino-6-chloro-indazole in 100 ml of pyrocarbonic acid diethyl ester is heated for 5 hours to 100° C, while stirring. After cooling, 100 ml of diethyl ether are added and 3-amino-6-chloroindazole-1-carboxylic acid ethyl ester is isolated, by filtration, in the form of colorless crystals (melting point: 190°–192° C; 60% of theory).

EXAMPLE 22

The reaction product of Example 21 is also obtained, in 70% yield, on reacting 0.2 mol of 3-amino-6-chloroindazole and 0.5 mol of pyrocarbonic acid diethyl ester in 500 ml of ethanol in 10 hours at 80° C.

EXAMPLE 23

The reaction product of Example 21 is also obtained, in 35% yield, on reacting 0.2 mol of 3-amino-6-chloroindazole and 0.22 mol of chlorocarbonic acid ethyl ester in 150 ml of pyridine in 1 hour at 20°–30° C.

EXAMPLE 24

The reaction product of Example 21 is also obtained, in 90% yield, on reacting 0.2 mol of 3-amino-6-chloroindazole 2-carboxylic acid ethyl ester in 80 ml of 2,4,6-trimethylpyridine in 15 minutes at 170° C.

EXAMPLE 25

The reaction product of Example 21 is also obtained, in 65% yield, on reacting 0.1 mol of 3-amino-6-chloroindazole and 0.12 mol of pyrocarbonic acid diethyl ester in 50 ml of quinoline in 1 hour at 20° ∝ 30° C and subsequently 30 minutes at 160° C.

EXAMPLE 26

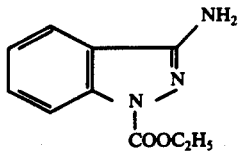

Analogously to Example 24, 0.07 mol of 3-aminoindazole-2-carboxylic acid ethyl ester in 50 ml of nitrobenzene gives 3-aminoindazole-1-carboxylic acid ethyl ester (melting point: 163°–165° C; 83% of theory) in 10 minutes at 210° C.

EXAMPLE 27

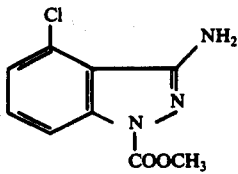

Analogously to Example 32, 0.05 mol of 3-amino-4-chloroindazole and 0.055 mol of chlorocarbonic acid methyl ester in 50 ml of pyridine give 3-amino-4-chloroindazole-1-carboxylic acid methyl ester (melting point: 190°–191° C; 58% of theory) in 1 hour at 20°–30° C.

EXAMPLE 28

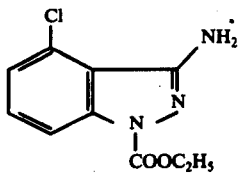

Analogously to Example 23, 0.1 mol of 3-amino-4-chloroindazole and 0.105 mol of chlorocarbonic acid ethyl ester in 80 ml of pyridine give 3-amino-4-chloroindazole-1-carboxylic acid ethyl ester (melting point: 167°–169° C; 62% of theory) in 1 hour at 50° C.

EXAMPLE 29

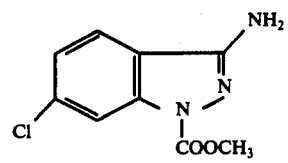

Analogously to Example 24, 0.05 mol of 3-amino-6-chloroindazole-2-carboxylic acid methyl ester in 50 ml of 2-methyl-pyridine gives 3-amino-6-chloroindazole-1-carboxylic acid methyl ester (melting point: 210°–211° C; 55% of theory) in 15 minutes at 125° C.

EXAMPLE 30

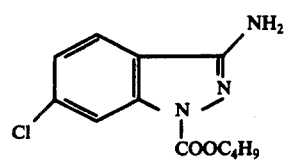

Analogously to Example 24, 0.04 mol of 3-amino-6-chloroindazole-2-carboxylic acid n-butyl ester in 25 ml of pyridine gives 3-amino-6-chloroindazole-1-carboxylic acid n-butyl ester (melting point: 139°–140° C; 61% of theory) in 15 minutes at 100° C.

EXAMPLE 31

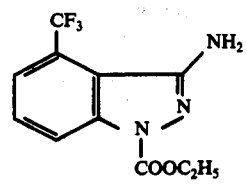

Analogously to Example 21, 0.06 mol of 3-amino-4-trifluoromethylindazole in 50 ml of pyrocarbonic acid diethyl ester gives 3-amino-4-trifluoromethylindazole-1-carboxylic acid ethyl ester (melting point: 185°–186° C; 68% of theory) in 2 hours at 75° C.

EXAMPLE 32

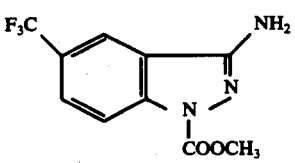

Analogously to Example 24, 0.065 mol of 3-amino-5-trifluoromethylindazole-2-carboxylic acid methyl ester in 70 ml of 4-methyl-pyridine gives 3-amino-5-trifluoromethylindazole-1-carboxylic acid methyl ester (melting point: 177°–178° C; 55% of theory) in 5 minutes at 140° C.

EXAMPLE 33

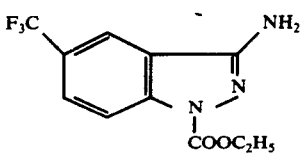

Analogously to Example 24, 0.175 mol of 3-amino-5-trifluoromethylindazole-2-carboxylic acid ethyl ester in 80 ml of 2,4,6-trimethyl-pyridine gives 3-amino-5-trifluoromethylindazole-1-carboxylic acid ethyl ester (melting point: 181°–183° C; 87% theory) in 30 minutes at 170° C.

EXAMPLE 34

The reaction product of Example 33 may also be obtained in 86% yield by reacting a mixture of 1.6 mol of 3-amino-5-trifluoromethylindazole-2-carboxylic acid ethyl ester, 370 ml of xylene and 20 ml of pyridine for 10 minutes at 135°–140° C.

EXAMPLE 35

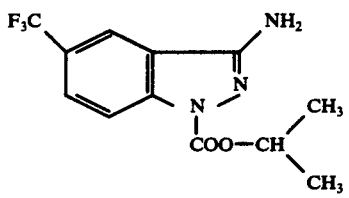

Analogously to Example 24, 0.04 mol of 3-amino-5-trifluoromethylindazole-2-carboxylic acid isopropyl ester in 25 ml of nitrobenzene gives 3-amino-5-trifluoromethylindazole-1-carboxylic acid isopropyl ester (melting point: 162°–163° C; 57% of theory) in 15 minutes at 210° C.

EXAMPLE 36

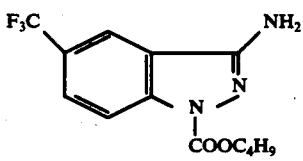

Analogously to Example 24, 0.02 mol of 3-amino-5-trifluoromethylindazole-2-carboxylic acid n-butyl ester in 15 ml of 1,2-dichlorobenzene gives 3-amino-5-trifluoromethylindazole-1-carboxylic acid n-butyl ester (melting point: 125°–127° C; 80% of theory) in 15 minutes at 175° C.

EXAMPLE 37

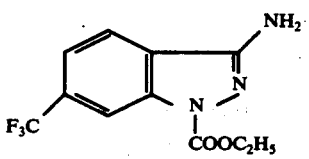

Analogously to Example 22, 0.04 mol of 3-amino-6-trifluoromethylindazole and 50 ml of pyrocarbonic acid diethyl ester in 25 ml of ethanol give 3-amino-6-trifluoromethylindazole-1-carboxylic acid ethyl ester (melting point: 168°–169° C; 64% of theory) in 2 hours at 80° C.

EXAMPLE 38

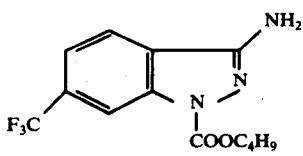

Analogously to Example 24, 0.03 mol of 3-amino-6-trifluoromethylindazole-2-carboxylic acid n-butyl ester in 20 ml of nitrobenzene gives 3-amino-6-trifluoromethylindazole 1-carboxylic acid n-butyl ester (melting point: 133°–134° C; 80% of theory) in 10 minutes at 200° C.

EXAMPLE 39

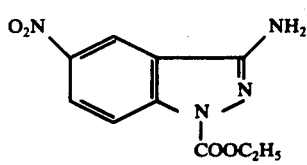

Analogously to Example 24, 0.05 mol of 3-amino-5-nitroindazole-2-carboxylic acid ethyl ester in 50 ml of nitrobenzene gives 3-amino-5-nitroindazole-1-carboxylic acid ethyl ester (melting point: 236°–237° C; 93% of theory) in 5 minutes at 210° C.

EXAMPLE 40

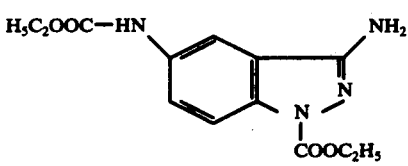

Analogously to Example 21, catalytic hydrogenation of 0.15 mol of 3-amino-5-nitroindazole with Raney nickel in tetrahydrofurane at 75° C, followed by reaction of the solution, which has been freed from the catalyst, with 0.6 mol of pyrocarbonic acid diethyl ester, in 2 hours at 50° C, gives 3-amino-5-ethoxycarbonylaminoindazole-1-carboxylic acid ethyl ester (melting point: 173°–174° C; 42% of theory).

EXAMPLE 41

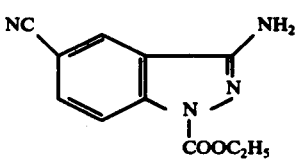

Analogously to Example 24, 0.07 mol of 3-amino-5-cyanoindazole and 0.08 mol of pyrocarbonic acid diethyl ester in 50 ml of 3-methyl-pyridine give 3-amino-5-cyanoindazole-1-carboxylic acid ethyl ester (melting point: 252° C; 57% of theory) in 15 minutes at 20° C followed by 10 minutes at 100° C.

EXAMPLE 42

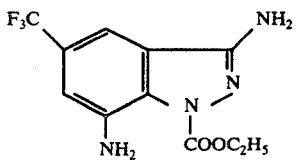

Analogously to Example 24, 0.1 mol of 3,7-diamino-5-trifluoromethylindazole-2-carboxylic acid ethyl ester in 30 ml of nitrobenzene gives 3,7-diamino-5-trifluoromethylindazole-1-carboxylic acid ethyl ester (melting point: 217°–218° C; 60% of theory) in 1 hour at 210° C.

EXAMPLE 43

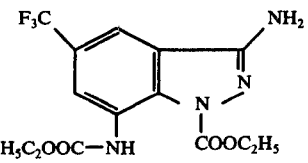

Analogously to Example 24, 0.025 mol of 3-amino-5-trifluoromethyl-7-ethoxycarbonylaminoindazole-2-carboxylic acid ethyl ester in 30 ml of dimethylformamide gives 3-amino-5-trifluoromethyl-7-ethoxycarbonylaminoindazole-1-carboxylic acid ethyl ester (melting point: 236°–237° C; 65% of theory) in 1 hour at 155° C.

EXAMPLE 44

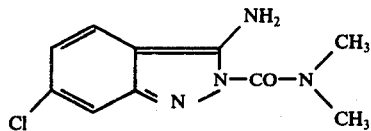

0.15 mol of dimethylcarbamic acid chloride is added dropwise, while stirring, to 0.1 mol of 3-amino-6-chloroindazole in 50 ml of pyridine, in the course of which the temperature rises to 45° C. After 1½ hours, 250 ml of water are allowed to run in and the reaction product is isolated by filtration. After dissolving the product in chloroform, filtering off a by-product of melting point 237°–238° C and evaporating the solution, 3-amino-6-chloroindazole-2-carboxylic acid dimethylamide (melting point: 178°–180° C; 58% of theory) is obtained.

EXAMPLE 45

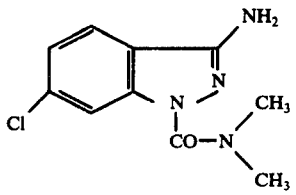

0.06 mol of 3-amino-6-chloroindazole-2-carboxylic acid dimethylamide in 25 ml of nitrobenzene is heated to 210° C for 15 minutes under $N_2$. Evaporation in vacuo and recrystallisation of the residue from ethanol gives 3-amino-6-chloroindazole-1-carboxylic acid-dimethylamide (melting point: 170°–172° C; 68% of theory).

EXAMPLE 46

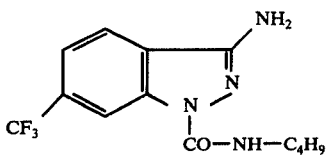

0.0275 mol of n butyl isocynate added dropwise to 0.025 mol of 3-amino-6-trifluoromethylindazole in 25 ml of chloroform, in the course of which the temperature rises to 30° C. The mixture is stirred for 3 hours at 20° C and finally for 15 minutes at 60° C, and after evaporation 3-amino-6-trifluoromethylindazole-2-carboxylic acid n-butylamide (melting point: 81°–83° C) is obtained; this is rearranged, by brief heating to 200° C in nitrobenzene, to 3-amino-6-trifluoromethylindazole-1-carboxylic acid n-butylamide (melting point 140°–142° C; 86% of theory).

EXAMPLE 47

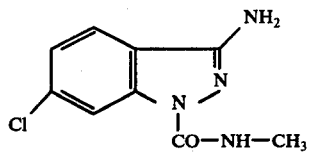

Analogously to Example 46, 0.1 mol of 3-amino-6-chloroindazole and 0.1 mol of methyl isocyanate in 100 ml of pyridine give 3-amino-6-chloroindazole-1-carboxylic acid methylamide (melting point: 148°–150° C; 50% of theory) in 30 minutes at 10°–15° C.

EXAMPLE 48

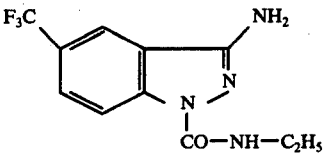

Analogously to Example 46, 0.05 mol of 3-amino-5-trifluoromethylindazole and 0.05 mol of ethyl isocyanate in 100 ml of pyridine give 3-amino-5-trifluoromethylindazole-1-carboxylic acid ethylamide (melting point: 131°–132° C; 47% of theory) in 1 hour at 10°–15° C.

EXAMPLE 49

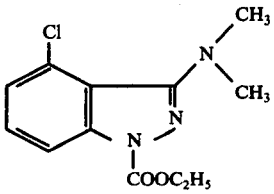

0.05 mol of 3-amino-4-chloroindazole-1-carboxylic acid ethyl ester and 0.125 mol of 40% strength formaldehyde solution in 50 ml of formic acid are heated to 100° C for 5 hours. After evaporation in vacuo and distillation of the residue, 3-dimethylamino-4-chloroindazole-1-carboxylic acid ethyl ester (boiling point$_{0.4}$ 160° C; melting point: 60°-62° C; 70% of theory) is obtained.

EXAMPLE 50

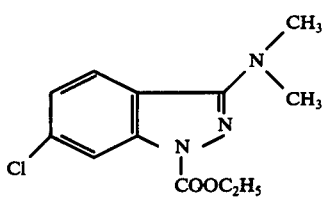

Analogously to Example 49, 0.1 mol of 3-amino-6-chloroindazole-1-carboxylic acid ethyl ester and 0.25 mol of 40% strength formaldehyde solution in 150 ml of formic acid give 3-dimethylamino-6-chloroindazole-1-carboxylic acid ethyl ester (melting point: 98°-100° C; 69% of theory) in 5 hours at 100° C.

EXAMPLE 51

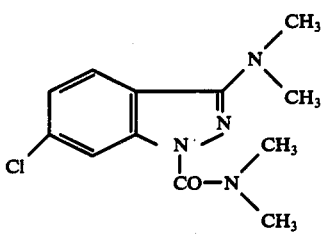

0.04 mol of 3-dimethylamino-6-chloroindazole and 0.04 mol of sodium amide in 50 ml of toluene are heated to the boil for 1 hour. 0.04 mol of dimethylcarbamic acid chloride is added dropwise at 60° C and this temperature is maintained for 7 hours, while stirring. After cooling, the solution is filtered and evaporated in vacuo. Distillation of the residue gives 3-dimethylamino-6-chloroindazole-1-carboxylic acid dimethylamide (boiling point$_{0.35}$ 170° C, melting point: 65°-66° C; 75% of theory).

EXAMPLE 52

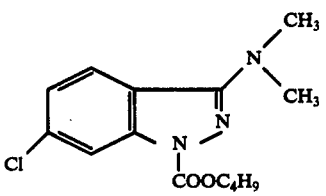

Analogously to Example 21, 0.01 mol of 3-dimethylamino-6-chloroindazole and 0.0125 mol of pyrocarbonic acid di-n-butyl; ester give 3-dimethylamino-6-chloroindazole-1-carboxyic acid n-butyl ester (melting point: 80°-81° C; 71% of theory) in 5 hours at 20° C.

EXAMPLE 53

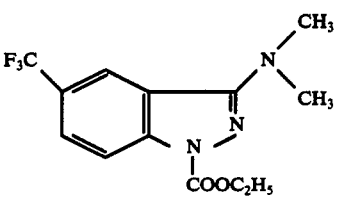

Analogously to Example 21, 0.025 mol of 3-dimethylamino-5-trifluoromethyl indazole and 0.0275 mol of pyrocarbonic acid diethyl ester give 3-dimethylamino-5-trifluoromethylindazole-1-carboxylic acid ethyl ester (boiling point$_{0.1}$ 110° C, melting point: 84°-86° C; 93% of theory) in 1½ hours at 70°-80° C.

EXAMPLE 54

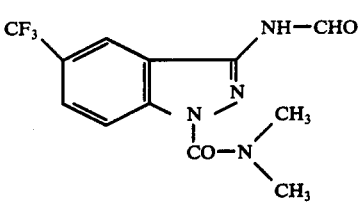

0.2 mol of 3-formylamino-5-trifluoromethylindazole and 0.05 mol of dimethylcarbamic acid chloride in 20 ml of pyridine are heated for 4 hours to 50° C. After cooling, 150 ml of water are allowed to run in and the reaction product which has crystallized out is isolated by filtration. Recrystallization from ethanol gives 3-formylamino-5-trifluoromethylindazole-1-carboxylic acid dimethylamide (melting point: 198°-200° C; 57% of theory).

EXAMPLE 55

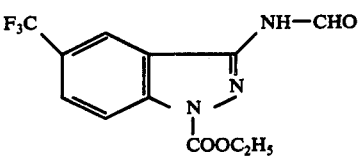

Analogously to Example 54, 0.05 mol of 3-formylamino-5-trifluoromethylindazole and 0.1 mol of chlorocarbonic acid ethyl ester in 100 ml of pyridine give 3-formylamino-5-trifluoromethylindazole-1-carboxylic acid ethyl ester (melting point: 185°-187° C; 65% of theory) in 3 hours at 30° C.

EXAMPLE 56

The reaction product of Example 55 is also obtained, in 78% yield, on reacting 0.1 mol of 3-amino-5-trifluoromethylindazole-1-carboxylic acid ethyl ester and 50 ml of formic acid in 5 hours at 100° C.

EXAMPLE 57

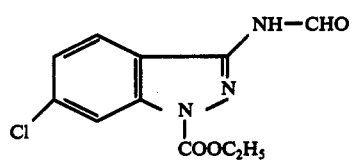

Analogously to Example 56, 0.085 mol of 3-amino-6-chloroindazole-1-carboxylic acid ethyl ester and 100 ml of formic acid produce 3-formylamino-6-chloroindazole-1-carboxylic acid ethyl ester in 3.5 hours at 100° C (melting point 227°-230° (decomposition), yield: 71% of theory).

EXAMPLE 58

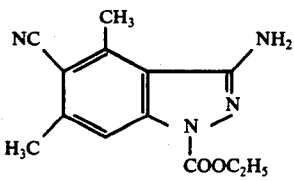

0.86 mol of 3-amino-4,6-dimethyl-5-cyanoindazole are stirred together with 0.13 mol of pyrocarbonic acid diethyl ester and 75 ml ethanol. The mixture is allowed to stand for two hours at room temperature and, after the addition of diethyl ether 3-amino-4,6-dimethyl-5-cyanoindazole-2-carboxylic acid ethyl ester is isolated (melting point: 235°–237° C, 90% of theory). After refluxing for 20 minutes in 250 ml of 1,2-dichloro-benzene, 3-amino-4,6-dimethyl-5-cyanoindazole-1-carbonic acid ethyl ester is obtained (melting point 240°–241° C; 95% of theory).

What is claimed is:

1. A compound selected from the group consisting of a 3-aminoindazole-1-carboxylic acid derivative of the formula:

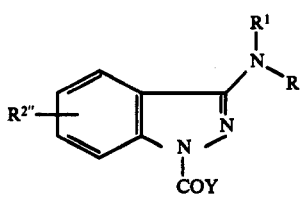

wherein
  Y is lower alkoxy, lower alkylamino or di(lower alkyl)amino wherein each alkyl or alkoxy group contains from 1 to 6 carbon atoms;
  R is hydrogen or lower alkyl of 1 to 6 carbon atoms;
  $R^1$ is hydrogen or lower alkyl of 1 to 6 carbon atoms or, when R is hydrogen, formyl; and
  $R^{2''}$ is chloro or trifluoromethyl in the 5- or 6-position of the indazole ring.

2. A compound according to claim 1 wherein both of R and $R^1$ are hydrogen, both of R and $R^1$ are methyl or R is hydrogen and $R^1$ is formyl.

3. A compound according to claim 1 wherein Y is methoxy, ethoxy, propoxy butoxy, methylamino, ethylamino or dimethylamino.

4. The compound according to claim 1 which is 3-amino-6-chloroindazole-1-carboxylic acid methyl ester.

5. The compound according to claim 1 which is 3-amino-6-chloroindazole-1-carboxylic acid ethyl ester.

6. The compound according to claim 1 which is 3-amino-5-chloroindazole-1-carboxylic acid ethyl ester.

7. The compound according to claim 1 which is 3-amino-6-chloroindazole-1-carboxylic acid dimethylamide.

8. The compound according to claim 1 which is 3-dimethylamino-6-chloroindazole-1-carboxylic acid ethyl ester.

9. The compound according to claim 1 which is 3formylamino-5-trifluoromethylindazole-1-carboxylic acid dimethylamide.

10. The compound according to claim 1 which is 3-amino-5-trifluoromethylindazole-1-carboxylic acid ethyl ester.

11. The compound according to claim 1 which is 3-amino-5-trifluoromethylindazole-1-carboxylic acid ethylamide.

12. The compound according to claim 1 which is 3-amino-5-trifluoromethylindazole-1-carboxylic acid methyl ester.

13. The compound according to claim 1 which is 3-amino-6-trifluoromethylindazole-1-carboxylic acid ethyl ester.

14. The method of achieving an analgesic, anti-inflammatory and/or antipyretic effect in humans and other warm blooded animals which comprises administering thereto an effective amount of a compound according to claim 1.

15. A pharmaceutical composition comprising a quantity of a compound according to claim 1 sufficient upon single or multiple administration to a human or other warm blooded animals to achieve analgesic, anti-inflammatory or antipyretic effect, in combination with a pharmaceutical carrier.

16. A compound selected from the group consisting of 3-aminoindazole-2-carboxylic acid derivative of the formula:

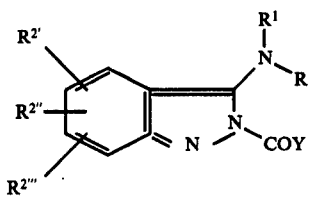

wherein
  Y is lower alkoxy, lower alkylamino or di(lower alkyl)amino wherein each alkyl or alkoxy group contains fromm 1 to 6 carbon atoms;
  R is hydrogen or lower alkyl of 1 to 6 carbon atoms;
  R is hydrogen or lower alkyl of 1 to 6 carbon atoms;
  $R^1$ is hydrogen or lower alkyl of 1 to 6 carbon atoms or, when R is hydrogen, formyl; and
  each of $R^{2'}$, $R^{2''}$ and $R^{2'''}$ is selected, independently of the others, from the group consisting of hydrogen, lower alkyl of 1 to 6 carbon atoms, lower alkoxy of 1 to 6 carbon atoms, nitro, amino, lower alkylamino of 1 to 6 carbon atoms, di(lower alkyl)amino wherein each alkyl group contains 1 to 6 carbon atoms, lower alkanoylamino of 1 to 6 carbon atoms, carbo(lower alkoxy)amino wherein alkoxy contains 1 to 6 carbon atoms, halo, trifluoromethyl, cyano and carbo(lower alkoxy) wherein alkoxy contains 1 to 6 carbon atoms,
and the pharmaceutically acceptable nontoxic salts thereof.

17. A compound according to claim 16 wherein both of R and R' are hydrogen, both of R and R' are methyl or R is hydrogen and R' is formyl.

18. A compound according to claim 17 wherein each of $R^{2'}$, $R^{2''}$ and $R^{2'''}$ is selected, independently of the others, from the group consisting of hydrogen, chloro, trifluoromethyl, nitro, amino, cyano, lower alkyl of 1 to 6 carbon atoms or carbo(lower alkoxy)amino wherein alkoxy contains 1 to 6 carbon atoms.

19. A compound according to claim 18 wherein each of $R^{2'}$ and $R^{2'''}$ is hydrogen and $R^{2''}$ is chloro or trifluoromethyl.

20. A compound according to claim 19 wherein $R^{2''}$ is chloro or trifluoromethyl in the 5- or 6-position of the indazole ring.

21. A compound according to claim 20 wherein Y is methoxy, ethoxy, propoxy or butoxy.

22. The compound according to claim 16 which is 3-amino-6-chloroindazole-2-carboxylic acid ethyl ester.

23. The compound according to claim 16 which is 3-aminoindazole-2-carboxylic acid ethyl ester.

24. The compound according to claim 16 which is 3-amino-5-chloroindazole-2-carboxylic acid ethyl ester.

25. The compound according to claim 16 which is 3-amino-5-trifluoromethylindazole-2-carboxylic acid methyl ester.

26. The compound according to claim 16 which is 3-amino-5-trifluoromethylindazole-2-carboxylic acid ethyl ester.

27. The compound according to claim 16 which is 3-amino-6-trifluoromethylindazole-2-carboxylic acid ethyl ester.

28. The compound according to claim 16 which is 3-amino-6-chloroindazole-2-carboxylic acid dimethylamide.

29. The method of achieving an analgesic anti-inflammatory and/or antipyretic effect in humans and other warm blooded animals which comprises administering thereto an effective amount of a compound according to claim 16.

30. A pharmaceutical composition comprising a quantity of a compound according to claim 16 sufficient upon single or multiple administration to a human or other warm blooded animals to achive analgesic, anti-inflammatory or antipyretic effect, in combination with a pharmaceutical carrier.

* * * * *